United States Patent [19]

Ahmed et al.

[11] Patent Number: 5,756,680
[45] Date of Patent: May 26, 1998

[54] SEQUENTIAL SEPARATION OF WHEY PROTEINS AND FORMULATIONS THEREOF

[75] Inventors: Salah H. Ahmed, Hayward; Vinit Saxena, Pleasanton; Zahid Mozaffar, Union City; Quirinus R. Miranda, San Jose, all of Calif.

[73] Assignee: Sepragen Corporation, Hayward, Calif.

[21] Appl. No.: 678,364

[22] Filed: Jul. 16, 1996

Related U.S. Application Data

[63] Continuation of Ser. No. 177,574, Jan. 5, 1994, abandoned.

[51] Int. Cl.$^6$ ............ C07K 16/04; C07K 14/47; C07K 1/36; A23C 9/14
[52] U.S. Cl. ............ 530/366; 426/41; 426/271; 426/583; 530/350; 530/364; 530/386; 530/394; 530/414; 530/416
[58] Field of Search ............ 530/350, 363, 530/364, 365, 366, 386, 394, 412, 414, 416, 832; 426/41, 271, 583

[56] References Cited

U.S. PATENT DOCUMENTS

| | | | |
|---|---|---|---|
| 4,614,653 | 9/1986 | Kakade | 426/2 |
| 4,803,089 | 2/1989 | Chaveron et al. | 426/239 |
| 4,834,994 | 5/1989 | Kuwata et al. | 426/271 |
| 4,865,729 | 9/1989 | Saxena et al. | 210/198.2 |
| 4,879,131 | 11/1989 | DeRahm | 426/583 |
| 5,077,067 | 12/1991 | Thibault | 426/271 |
| 5,149,647 | 9/1992 | Burling | 435/192 |
| 5,179,197 | 1/1993 | Uchida et al. | 530/366 |
| 5,223,281 | 6/1993 | Kulczjcki et al. | 426/42 |

OTHER PUBLICATIONS

Girardet et al. "Effects of Chromatographic Parameters on the Fractionation of Whey Proteins by Anion Exchange FPLC"Milchwissencharft 44(11) 692–696 1989.

Høst et al. "Prospective Estimation of IgG,IgG Subclass & IgE Antibodies to Dietary Proteins In Infants w/Cow Milk Allergy"Allergy 47 (3) 218–229 1992

Manji et al. "Rapid Separation of Milk Whey Proteins by Anion Exchange Chromatography"J. Dairy Sci 68 3176–3179 1985.

*Primary Examiner*—Mindy Fleisher
*Assistant Examiner*—Nancy J. Degen
*Attorney, Agent, or Firm*—Medlen & Carroll

[57] ABSTRACT

A method is disclosed for the sequential separation of whey proteins using radial-flow chromatography. Different buffer systems adjusted to suitable pH and ionic strength are utilized in the separation process. The method separates at least five different proteins from whey. Infant feeding formulas, and other food formulations are also disclosed incorporating therein in different proportions various proteins separated from the whey.

11 Claims, 3 Drawing Sheets

ELUTION PATTERN OF WHEY PROTEINS SHOWING PEAK 4

SEQUENTIAL SEPARATION OF WHEY PROTEINS AND FORMULATIONS THEREOF

This is a continuation of application Ser. No. 08/177,574 filed on Jan. 5, 1994, now abandoned.

FIELD OF THE INVENTION

The present invention is related to the separation of whey proteins, particularly to the sequential separation of whey proteins using chromatography and to food related and pharmaceutical formulations using separated whey proteins.

BACKGROUND OF THE INVENTION

It is well known that the dry content of cow's milk is about 12.5% of which 3.4% constitute total proteins, 3.5% comprise fat components, 4.7% lactose and 0.9% ash. The protein component consists mainly of casein and whey proteins. Other minor components include non-proteinaceous nitrogen compounds, protease peptones, and other minor enzyme proteins.

In the cheese industry, milk proteins are separated into caseins and whey proteins, mainly by two types of precipitation techniques—rennet precipitation and acid precipitation. In rennet precipitation, rennin is added to warm milk (30°–35° C.). The caseins are precipitated leaving the whey proteins in solution. This type of whey is referred to as sweet whey. Acid precipitation is carried out at the isoelectric point of milk which is 4.7 by using a suitable acid. The whey resulting from acid precipitation is referred to as acid-whey. The choice of the method depends on the desired cheese product.

Whey which is a byproduct of the cheese industry has a high nutritional value because of the many valuable proteins in its composition. However, until recently, a major portion of commercially produced whey was discarded, causing major environmental pollution problems. With the advent of stricter environmental controls and regulations and the availability of more recent techniques like membrane separation including ultrafiltration and reverse osmosis, whey proteins and other products constituted therefrom have become increasingly important in satisfying the needs of the pharmaceutical, dietetic and food industries. Research efforts with varying degrees of success in the area of the isolation of individual proteins from whey and formulations constituted therefrom abound in the dairy and related industries.

The following patents exemplify the various prior art efforts to isolate individual proteins and other constituents from whey and food and pharmaceutical products derived therefrom.

U.S. Pat. No. 5,077,067 issued Dec. 31, 1991, to Philippe A. Thibault discloses a process for the selective and quantitative removal of lactoglobulins from whey proteins.

U.S. Pat. No. 5,055,558 issued Oct. 8, 1991 to Emilia Chiancone and Maurizio Gattoni describes a method for the selective extraction of β-lactoglobulin from whey or milk by subunit exchange chromatography.

U.S. Pat. No. 4,791,193, issued Dec. 13, 1988, to Shigeo Okonogi et al., is directed to a method for the preparation of pure lactoferrin from whey or skim milk.

U.S. Pat. No. 4,668,771, issued May 26, 1987, to Hiroshi Kawakami et al., provides a method for the isolation and purification of bovine lactoferrin.

U.S. Pat. No. 4,997,914 issued Mar. 5, 1991 to Hiroshi Kawakami et al., describes a method for the separation and purification of lactoferrin by adsorption chromatography.

U.S. Pat. No. 4,820,348 issued Apr. 11, 1989 to Matti Harju is directed to a chromatographic method for the separation of lactose from milk.

U.S. Pat. No. 4,446,164 issued May 1, 1984 to Roy A. Brog relates to milk like compositions constituted from sweet whey base with additives like soluble proteins, edible vegetable oils, non-fat dry milk solids, sugar or synthetic sweeteners included therein.

U.S. Pat. No. 5,085,881 issued Feb. 4, 1992, to Hans G. Moeller is describes a process for separating fractions from dried milk or milk products for use as food stuffs or food or pharmaceutical adjuvants.

U.S. Pat. No. 5,093,143 issued Mar. 3, 1992 to Horst Behr and Friedrich Manz deals with nutrient compositions which simulate milk and are rich in energy and calcium content but poor in albumin and phosphorus.

U.S. Pat. No. 4,202,909 issued May 13, 1980 to Harold T. Pederson, Jr., describes a process for the treatment of whey to produce pure lactose and salt products.

U.S. Pat. No. 5,008,376 issued Apr. 16, 1991 to Robin C. Bottomley discloses a process for producing a whey fraction with a high concentration of alpha-lactalbumin by ultrafiltration technology.

U.S. Pat. No. 3,969,337 issued Jul. 13, 1976 to Karl Lauer et al., discloses a method for the chromatographic fractionation of whey.

As the foregoing patents and other literature articles demonstrate, although different laboratory and commercial processes are available for the separation, removal, concentration, and/or purification of selected whey proteins, these prior art methods result in the destruction or disposal of all but one selected protein from the whey, thereby wasting the other valuable proteins therefrom. None of these prior art methods achieve the separation of various proteins from whey in a single process step. It would be desirable, therefore, to provide a method for the continuous and sequential separation of various proteins from whey in a one or two step separation process.

Accordingly, it is an object of the present invention to provide a separation technique which effects a complete sequential separation of whey proteins in one or two process steps.

Another object of the present invention is to provide a separation technique for the sequential and continuous separation of whey proteins which is suitable for laboratory as well as commercial applications using radial flow chromatography technology.

Yet another object is to provide different buffers which are mild enough to use in sequentially separating whey proteins without denaturing them.

Still another object is to provide a separation technique applicable for food and pharmaceutical uses of whey proteins.

Another object of the invention is to provide dietary and pharmaceutical formulations comprising various separated whey proteins in differing proportions.

Additional objects, advantages and novel features of the invention will be set forth in part in the description which follows and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objectives and in accordance with the purpose and principles of the invention as set forth herein, the present invention basically provides a process for the sequential separation of at least five different proteins from whey and incorporating these separated whey proteins into pharmaceutical and food formulations. The process of the invention is directed to the continuous, sequential separation of whey proteins by chromatography, comprising adsorbing the proteins in liquid whey on a suitable separation medium packed in a chromatographic column and sequentially eluting IgG, β-Lg, α-La, BSA and lactoferrin fractions with buffers at suitable pH and ionic strength. Even though both axial and radial flow chromatography may be utilized, a horizontal flow column is particularly suitable for the process of this invention. The whey proteins separated by the process of the invention include β-lactoglobulin (β-Lg), α-lactalbumin (α-La), bovine serum albumin (BSA), immunoglobulin (IgG) and Lactoferrin (L-Fe). The various formulations of the invention for dietary or pharmaceutical applications incorporate these separated proteins in various proportions.

DETAILED DESCRIPTION OF THE INVENTION

According to the process of the invention, a sample of a starting material selected from pasteurized sweet whey, pasteurized acid whey, non-pasteurized acid whey obtained as a by-product of cheese manufacture, or whey protein concentrate, prepared from the pasteurized or non-pasteurized whey by known techniques such as reverse osmosis (RO) or ultrafiltration (UF) is loaded on to a chromatographic column, preferably a horizontal flow chromatographic column, packed with either an acidic or basic, cationic or anionic resin material such as macro-prep high S or Q. The whey, concentrated whey or whey protein concentrate may be subjected to pre-separation procedures such as de-ashing through electrodialysis or ion exchange, clarification to remove casein fines, and/or microfiltration for separating colloidal and suspended particles including fat residues.

The various whey components were then eluted and separated according to the protocols described in the following examples.

EXAMPLE 1
Sequential Separation Of Sweet Whey Proteins

Commercial whey, a by-product of mozzarella cheese manufacture, was initially clarified to remove casein fines, centrifuged to remove milk fat residue, pasteurized at 162° F. for about 18 seconds, and chilled to 40° F. by passing it through HTST plate heat exchangers. 1000 ml of this skimmed commercial sweet whey at pH 6.4 and 6.2% total solids, was pH adjusted to 3.8 with acetic acid at 40° F. The composition of this whey product used in this experimental example is presented in Table I.

TABLE I

| WHEY | | | |
|---|---|---|---|
| Components | Percentage | Protein Composition | |
| Total solids | 6.2 | β-lactoglobulin | 0.29% |
| Lactose | 4.5 | α-lactalbumin | 0.13% |
| Protein | 0.8 | Serum casein | 0.21% |
| Fat | 0.08 | Immunoglobulin | 0.06% |
| Ash | 0.77 | Lipoprotein | 0.06% |
| Lactic Acid | 0.05 | Bovine serum albumin | 0.03% |
| | | Lactoferrin | 0.02% |

The whey was then passed through a 250 ml radial flow chromatographic column prepacked with a strong S cation exchange resin and equilibrated with 0.05M acetate buffer at pH 3.8. All the whey proteins were bound to the resin matrix, and the effluent containing non-protein components including lactose, minerals, lactic acid, and non-protein nitrogenous components was allowed to pass through. The resin with the bound proteins was then washed with 0.05M acetate buffer at pH 3.8 to a preset UV baseline. The various bound proteins were then sequentially eluted in accordance with the following protocol:

Immunoglobulin (IgG) and β-lactoglobulin (β-Lg) were eluted in sequential order with a buffer at pH 4.0 containing 0.1M sodium acetate and 0.5M sodium chloride.

The column was then reconditioned and equilibrated with 0.05M sodium acetate buffer at pH 4.0, to bring the conductivity back to the base line.

α-Lactalbumin (α-La) fraction was eluted with a pH 5.0 buffer containing 0.1M sodium acetate and 0.1M sodium chloride. The column was again reconditioned with a pH 5.0 buffer containing 0.05M sodium acetate to bring the conductivity back to the initially established base line. Bovine serum albumin (BSA) was then eluted with a 0.05M phosphate buffer at pH 7.0. Thereafter, lactoferrin (LF) was eluted at pH 7.5 with a buffer containing 0.05M sodium phosphate and 0.5M sodium chloride.

The column was again regenerated by washing it with a solution containing 0.2M sodium hydroxide and 1M sodium chloride, followed by a wash with a 20% ethanol (EtOH) solution to sterilize the column and equilibrated with acetate buffer at pH 3.8 for reuse.

A flow diagram showing the elution protocol is presented in Table II below.

TABLE II

Flow Diagram Of Elution Protocol

Whey
(1000 ml skimmed sweet whey from mozzarella cheese manufacture- at 40–50° F., pH 6.4)

↓ pH adjusted to 3.8
(with acetic acid)

↓

TABLE II-continued

Flow Diagram Of Elution Protocol

TABLE II-continued

Flow Diagram Of Elution Protocol

Re-equilibration (with 0.05M Na Acetate at pH 3.8)
↓
Repeat Sequence

Figure 1:
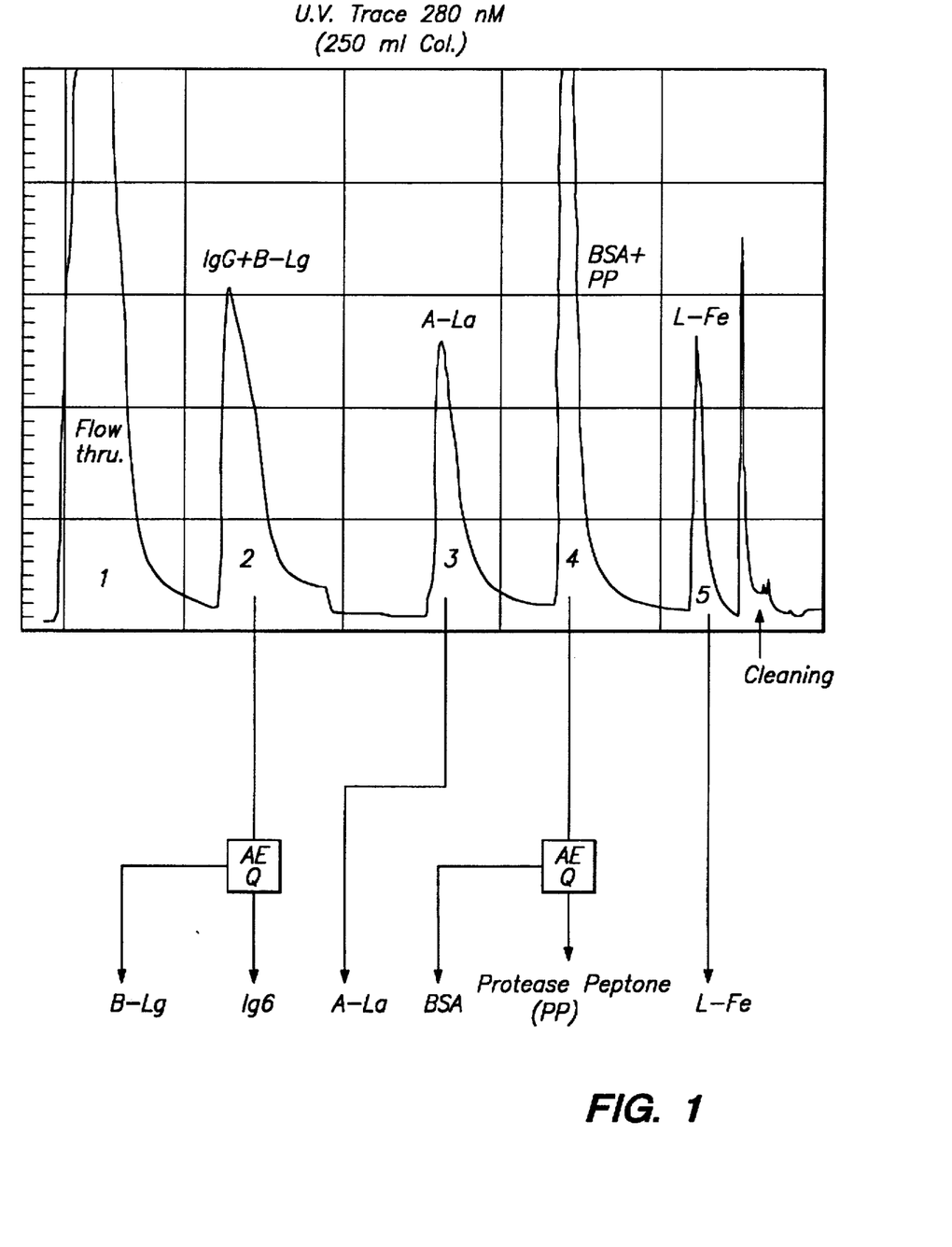
FIG. 1 is a graphic representation of the elution pattern of the various proteins in accordance with this invention.

Fractions of each of the eluted proteins were collected in terms of elution "peaks" for further separation, concentration, and other treatment protocols. The elution sequence with the different protein peaks in terms of their UV absorption at 280 nm is presented in FIG. 1. Protein identification of each peak was monitored by sodium dodecyl sulfate-polyacrylamide gel electrophoresis (SDS-PAGE), as known in the art. Protein recovery as monitored by bio-rad and gel scan assays at various stages of the elution scheme is presented in Tables III and IV.

TABLE III

Summary of Bio-Rad Assay Data

| | | |
|---|---|---|
| (#0) | Column Load 1.0 L treated whey<br>4.3 mg/ml total protein | 4.3 g loaded |
| (#1) | Column Flow-Through 1.65 L<br>0.2 mg/ml total protein | 0.3 g (7%) |
| (#2) | β-Lg + IgG Fraction 2.4 L<br>1.2 mg/ml total protein | 2.9 g (67%) |
| (#3) | α-La Fraction 1.25 L<br>0.5 mg/ml total protein | 0.6 g (14%) |
| (#4) | BSA Fraction 1.625 l<br>0.3 mg/ml total protein | 0.4 g (9%) |
| (#5) | L-Fe Fraction 0.625 L<br>0.09 mg/ml total protein | 0.05 g (1%) |
| (#6) | Wash 1 1.6 L<br>0.03 mg/ml total protein | 0.05 g (1%) |
| (#7) | Wash 2 0.4 L<br>0.09 mg/ml total protein | 0.04 g (1%) |
| Total Recovery = 4.3 g = 100% accountability | | |

TABLE IV

Summary Of Gel Scan Data

| | | |
|---|---|---|
| Gel #1<br>Column Load | $R^2 = 0.98$<br>1.0 L treated whey<br>4.5 mg/ml total protein<br>Approximate % Composition | 4.5 g loaded |
| | 76% β-Lg<br>17% α-La<br>2% BSA<br>3% IgG<br>2% Other | No protein eluted in flow-through |
| Gel #2<br>Volume = 2.4 L | $R^2 = 0.99$<br>β-Lg and IgG Fraction<br>1.2 mg/ml total protein<br>94% β-Lg | 2.9 g recovered (64%) |

TABLE IV-continued

Summary Of Gel Scan Data

| | | |
|---|---|---|
| Gel #3<br>Volume = 1.25 L | 2% IgG<br>R3 = 0.993<br>α-La Fraction<br>0.03 mg/ml total protein<br>94% α-La | 0.4 g recovered (9%) |
| Gel #4<br>Volume = 1.625 L | R3 = 0.991<br>BSA Fraction      0.625 L L-Fe Fraction<br>0.08 mg/ml total protein in BSA Fraction<br>62% BSA recovery (minimum)<br>0.05 mg/ml total protein in L-Fe Fraction<br>45% L-Fe recovery (minimum) | 0.13 g (3%)<br>0.03 g (1%) |

EXAMPLE 2
An Alternative Protocol For Elution Of Whey Proteins

Figure 2:
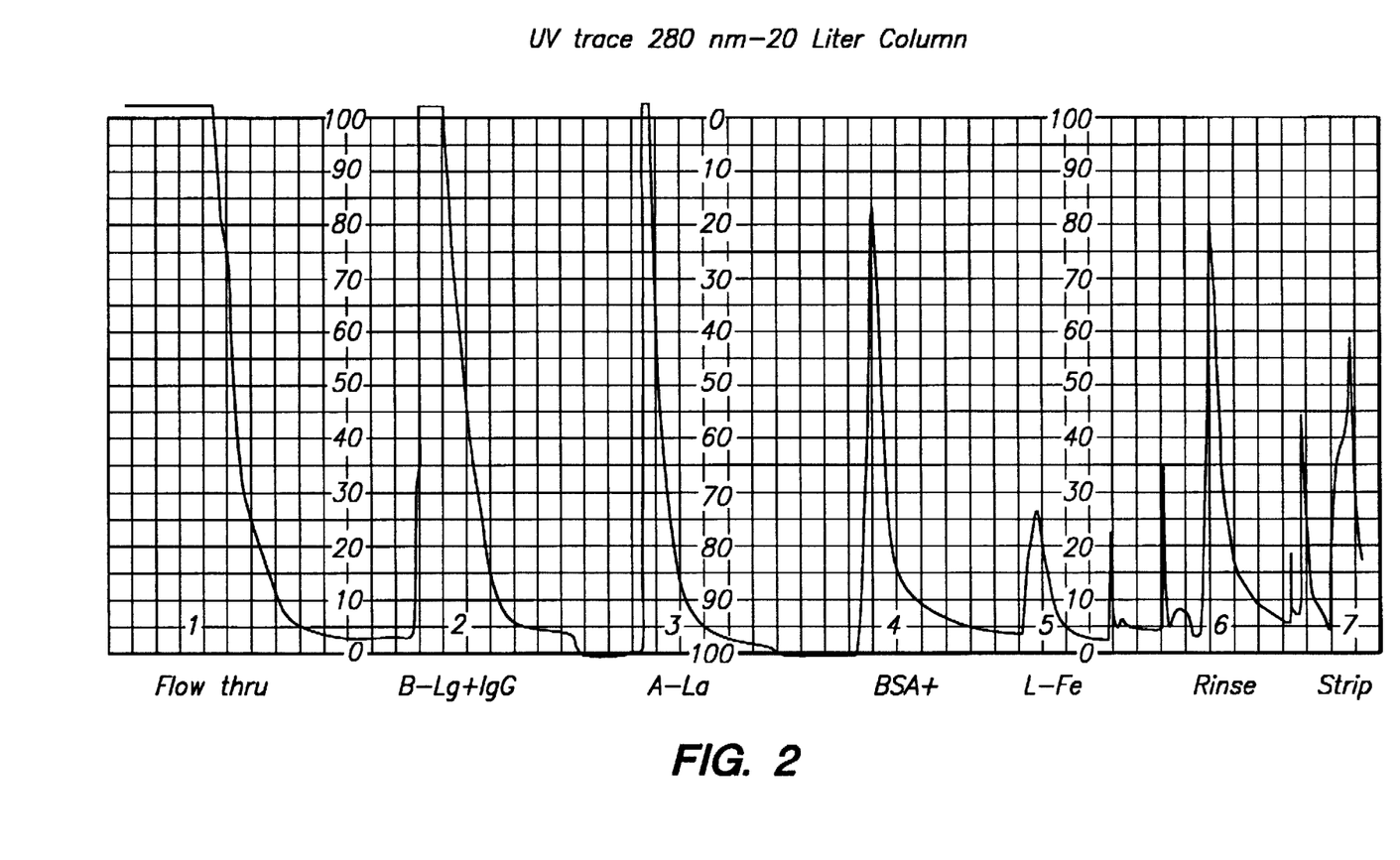
FIG. 2 presents an elution profile of separated proteins vs. time.

A 20 liter RFC column was packed with a macro-prep 50 S resin. The column was then conditioned, equilibrated, loaded, eluted and reconditioned in exactly the same manner as described in Example 1 above, except that the flow rates, volume of whey loaded on to the column, flow rates and buffer volumes were varied. Protein elution peaks were monitored at 280 nm using a uv spectrophotometer. A graphical trace of the eluted proteins with their relative concentrations is presented in FIG. 2. The proteins eluted with their respective percentages of purity are shown in Tables V and VI.

TABLE V

Protein Yields In Eluate Fractions
(20 L column; Flow Rate 8 L/min; Whey Load 80 L)

| | Protein<br>(g/L) | Volume<br>(L) | Protein Yield<br>Load (g) | % |
|---|---|---|---|---|
| Whey Load | 8.8 | 80 | 704 | — |
| Flow Through (P-1) | 0.9 | 97 | 87 | 12 |
| β-La + IgG (P-2) | 2.8 | 89 | 249 | 35 |
| α-Lactalbumin (P-3) | 1.1 | 94 | 103 | 15 |
| BSA (P-4) | 1.1 | 102 | 112 | 16 |
| Lactoferrin (P-5) | 0.9 | 45 | 41 | 6 |
| Rinse (P-6) | 0.8 | 22 | 18 | 3 |
| Stripping Solution (P-7) | 1.2 | 29 | 35 | 5 |

Protein Recovery: 84%; Protein Accountability: 92%

TABLE VI

| Protein Purity (Gel Scan) | % |
|---|---|
| β-Lactoglobulin | 82 |
| Immunoglobulin | 11 |
| α-Lactalbumin | 84 |
| Bovine Serum Albumin | 59 |
| Lactoferrin | 52 |

EXAMPLE 3
Preparation Of An Anionic Exchange Resin Column

A 250 ml RFC column was packed with a strong base, anionic exchange resin—macro-prep 50 Q—and conditioned with 0.2M NaOH+1M NaCl at a flow rate of 100 ml/min for 10 minutes. The column was then equilibrated with 0.01M sodium phosphate at pH 6.90 at a flow rate of 100 ml/min for 10 minutes. This column was then used to separate immunoglobulins (IgG) from β-Lactoglobulin eluted as overlapping peaks from Examples 1 and 2 above. This mixture may be incorporated into dietary formulations or used for further separation of the two protein components.

EXAMPLE 4
Separation Of Immunoglobulins (IgG) from β-Lactoglobulin

The eluate represented by peak 2, collected from the fractionated material from the process described in Example 1, and containing IgG and β-Lg at pH 4.0, was passed through a 10,000 molecular weight cut-off UF membranes for concentrating the proteins and for reducing the buffer salt concentration and thereby, the ionic strength of the solution. The proteins were further concentrated to 5× their initial eluted concentrations and buffer salt concentrations were reduced to about one-fourth their eluting concentration by diafiltration with distilled water. The diafiltered and concentrated protein solution was pH adjusted to 6.9 with a 2.0M solution of NaOH. Two liters of this protein solution at pH 6.9 was loaded on to the pre-conditioned RFC column as described in Example 3, at a flow rate of 100 ml/min. The column was washed with 0.01M sodium phosphate buffer at pH 6.9 to establish a UV baseline. IgG which did not bind to the resin passed through the column with the wash and was collected for further processing. The adsorbed β-Lg was then eluted from the column with 0.05M sodium citrate buffer at pH 3.0 and collected. The column was rinsed with distilled water, stripped of residual proteins with 0.2M NaOH+1M NaCl solution, followed by 20% EtOH and again reequilibrated with sodium phosphate buffer at pH 6.9, in preparation for the next cycle.

EXAMPLE 5
Separation And Isolation Of BSA

Figure 3:
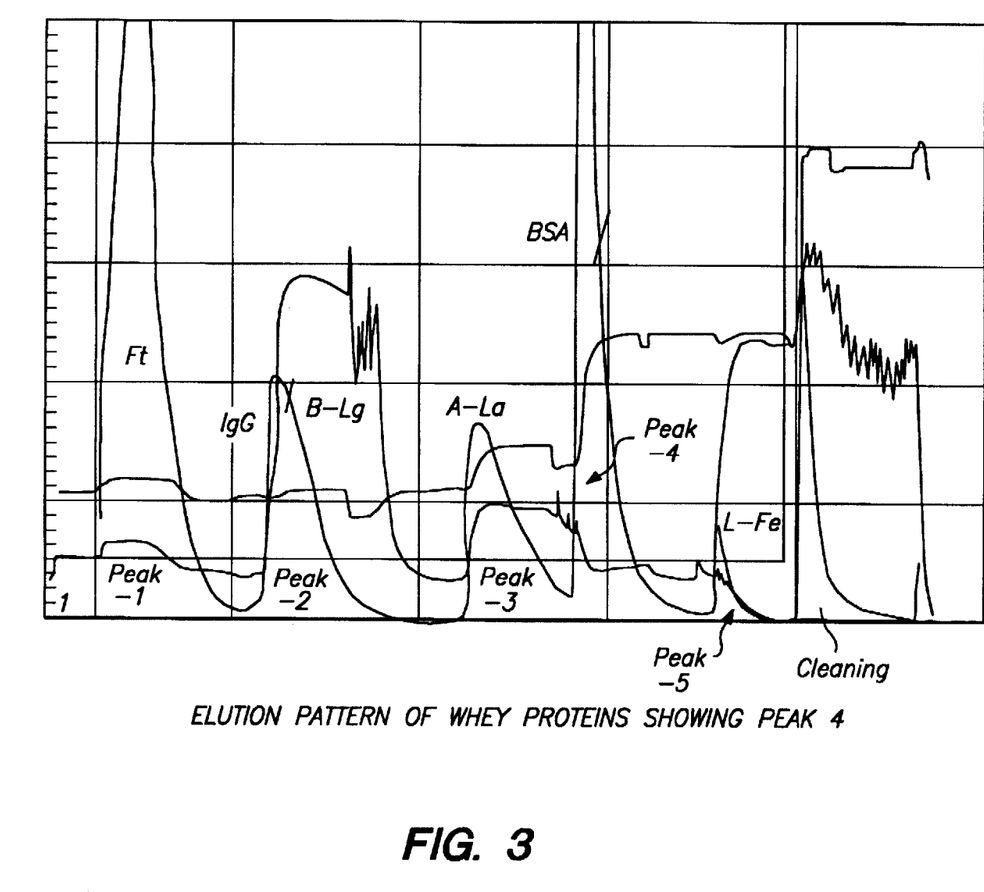
FIG. 3 represents the elution pattern and the location of peak 4.

The eluate represented by peak 4, collected from the fractionated material from the process described in Example 1, and containing BSA, and protease peptone at pH 7.0 was concentrated and diafiltered as described in Example 4, then pH adjusted to 5.5 with acetic acid. A 250 ml RFC column prepared as described in Example 4 was rinsed with distilled water at a flow rate of 100 ml/min. Two liters of the protein solution were loaded onto the column as described earlier. The column was again flushed with distilled water at a flow rate of 100 ml/min to elute the nonadsorbed protease peptone and to establish a stable UV baseline. The eluate containing the protease peptone was collected for further use. The adsorbed BSA was thereafter eluted with sodium phosphate buffer containing 0.2M sodium chloride at pH 7.0. FIG. 3 represents the elution pattern and the location of peak 4.

EXAMPLE 6
Elution And Separation Of β-Lactoglobulin From Liquid Whey

A 250 ml radial-flow chromatographic column packed with a strong base anionic exchange resin (macro-prep 50 Q)

was washed and regenerated according to manufacturer's instructions. The column was then equilibrated with 0.05M sodium phosphate (tribasic) at pH 7.5 at a flow rate of 100 ml/min for 10 min. pH ranges of 7.0 to 8.0 did not significantly affect the elution pattern. Two liters of clarified, skimmed, pasteurized sweet whey from mozzarella cheese manufacture, chilled to 40° F. were pH adjusted to 8.0 with 5M sodium hydroxide, were circulated through the pre-prepared column at 75 mils/min for equilibration. Flow rates in the range of $50 \geq 100$ ml/min were utilized. Then a 1 to 3 liter sample of whey to be analyzed was loaded on to the column and the column eluted with the loading buffer— 0.05M sodium phosphate at pH 7.5. Under the conditions utilized, all whey proteins except β-lactoglobulin are positively charged. β-lactoglobulin being negatively charged, is bound to and retained by the anionic exchange resin. The effluent containing non-bound proteins [α-Lactalbumin (α-La), Immunoglobulin (Ig-G), bovine serum albumin (BSA) and lactoferrin (L-Fe)] was allowed to pass through the column, collected and stored at 40° F. for further processing.

The adsorbed B-lactoglobulin was then eluted from the column with a pH 7.5 buffer containing 0.05M sodium phosphate and 0.5M sodium chloride. This eluate containing β-lactoglobulin may be processed further to prepare a shelf stable product in the same manner as described in Example 8 below.

The column was washed with 1M sodium chloride at a flow rate of 125 ml/min for about four column volumes (2 liters), stripped with 1M sodium hydroxide at the same flow rate, regenerated with 1M sodium chloride at a flow rate of 100 ml/min for about five column volumes (2½liters) sanitized with 200 ppm sodium hypochlorite at 100 ml/min for about four column volumes (2 liters) and then equilibrated with the loading buffer in preparation for the next cycle.

EXAMPLE 7
Elution And Sequential Separation Of Four Proteins From A Non-β-Lactoglobulin Fraction Of Liquid Whey The flow-through fraction from Example 6, containing 0.55% protein, was passed through a 10,000 molecular weight cut-off, spiral ultra-filtration membrane to a 35% of the original volume, removed as a permeate for the purpose of partial protein concentration and also for reduction of soluble salts. This pre-treatment procedure facilitates the optimum absorption and sequential desorption of Ig-G, α-La, BSA and L-Fe protein fractions as outlined in Example 1. The prepared flow-through was pH adjusted to 3.8 with acetic acid and 1500 ml sample of it was loaded onto a 250 ml RFC column packed with a strong S-cationic exchange resin and pre-equilibrated with 0.05M sodium acetate buffer at pH 3.8. Washing, sequential elution and regeneration steps as outlined in Example 1 were followed. The eluted protein fractions were individually passed through the appropriate molecular weight cut-off—50000 MW cut-off membrane for Ig-G, L-Fe and BSA and 10,000 MW cut-off membrane for α-La—to concentrate proteins and eliminate salt residues. It was then processed further to a finished product as outlined in Example 8.

EXAMPLE 8
Flow Diagram Showing Preparation Of Final Product

The whey protein fractions or the separated and purified proteins and the non-proteinaceous eluants may be incorporated into dietary and pharmaceutical formulations in appropriate proportions. Such formulations include but are not limited to infant formulas, fat substitutes, foaming agents, egg white substitutes, animal feed substitutes and the like.

EXAMPLE 9
Infant Formulas

In the infant formulas constituted in accordance with this invention, the casein and whey fractions of cow's milk were modified to achieve a composition simulating human milk to a significantly larger degree than prior art compositions and commercial products. The infant formulas of the present invention contain whey proteins at levels similar to those in human milk. This was achieved by producing a whey protein ingredient mix containing the type and ratio of whey proteins of human milk.

Commercially available infant formulas are constituted from whole cow's milk, mostly because of its availability on a large scale. Other additives or adjuvants may be included. These formulas are manufactured either in powder, concentrated or ready to feed preparation. They consist, for the most part, of non-fat milk solids, vegetable oils and carbohydrate sweeteners such as lactose, corn syrup solids and sucrose. These formulas may also be fortified with vitamin C, vitamin D, iron and fluoride. Table VII shows the typical compositions of a few exemplary commercial infant formulas in comparison to one exemplary formula of the present invention. Levels of vitamins, minerals and other fortifiers in the formulation of the present invention are adjusted to simulate human milk and to meet nutritional requirements of infants.

TABLE VII

Composition Range Of Some Commercial Infant Formulas Compared To One Exemplary Formulation Of The Present Invention

| Nutrients | Commercial Infant Formulas (Similac, Alimentum, Good Start, Gerber etc.) Per 5 Oz Prepared Feed (~12.5% solids) | Ingredients | Formula Of Present Invention Per 5 oz Prepared Feed (~12.5% solids) | Ingredients |
|---|---|---|---|---|
| Protein | 2.14–2.75 g | NFDM*-Casein hydrolysate-whey protein composition | 1.1–2.50 g | Dry or wet mix of purified, selected proteins |
| Fat | 5.1–5.54 g | veg, coconut, soy, palm, safflower, sun flower oil etc. | 4.30–6.48 g | veg oils, milk fat |
| Carbohydrate | 10.2–11.0 g | lactose, sucrose | 10.19–10.50 g | lactose |
| Water | 133–135 g | | 15–130 g | |
| Linoleic Acid | 850–1600 mg | | 1200–1300 mg | |
| Vit. A | 300 IU | | 300–350 IU | |
| Vit. D | 45–60 IU | | 50–60 IU | |
| Vit. E | 2.0–3.0 IU | | 2.2–2.7 IU | |
| Vit. C | 9 mg | | 7–9 mg | |
| Vit. K | 8–15 mcg | | 8–10 mcg | |
| Vit. B1 | 60–100 mcg | | 25–100 mcg | |
| Vit. B2 | 90–150 mcg | | 50–150 mcg | |
| Vit. B6 | 60–75 mcg | | 20–60 mcg | |
| Vit. B12 | 0.22–0.45 mcg | | 0.10–0.25 mcg | |
| Niacin | 750–1350 mcg | | 300–1100 mcg | |
| Folic Acid | 9–15 mcg | | 7–15 mcg | |
| Pantothenic Acid | 450–750 mcg | | 330–450 mcg | |
| Biotin | 2.2–4.5 mcg | | 2–4 mcg | |
| Choline | 8–16 mg | | 10–16 mg | |
| Inositol | 4.7–18 mg | | 4.5–5.5 mg | |
| Calcium | 64–105 mg | | 47–73 mg | |
| Phosphorus | 36–75 mg | | 21–56 mg | |
| Magnesium | 6.0–7.5 mg | | 4.4–6.0 mg | |
| Iron | 0.5–1.8 mg | | 0.04–1.8 mg | |
| Zinc | 0.75 mg | | 0.25–0.75 mg | |
| Manganese | 5–30 mcg | | 5–10 mcg | |
| Copper | 75–90 mcg | | 75–90 mcg | |
| Iodine | 8–15 mcg | | 9–12 mcg | |
| Sodium | 24–44 mg | | 25–40 mg | |
| Potassium | 98–118 mg | | 75–110 mg | |
| Chloride | 59–80 mg | | 59–80 mg | |
| Cholesterol | — | | 18–25 mg | |

*NFDM-non-fat dry milk solids

However, due to the large differences in the protein compositions of cow's milk and human milk, some infants show different degrees of intolerance to cow's milk and food formulas constituted therefrom. A comparison of the composition of cow's milk with that of human milk is presented in Table VII and a comparison of their protein content is presented in Table IX.

TABLE VIII

Comparison of Cow's Milk With Human Milk

| Per 100 g | Cow | Human |
|---|---|---|
| Water g. | 89.99 | 87.5 |
| Food Energy kcal. | 61 | 70 |
| Protein (N × 6.38) g. | 3.29 | 1.03 |
| Fat g. | 3.34 | 4.38 |
| Carbohydrate (total) g. | 4.66 | 6.89 |
| Fiber g. | 0 | 0 |
| Ash g. | 0.72 | 0.2 |

TABLE VIII-continued

Comparison of Cow's Milk With Human Milk

| Per 100 g | Cow | Human |
|---|---|---|
| Minerals | | |
| Calcium mg. | 119 | 32 |
| Iron mg. | 0.05 | 0.03 |
| Magnesium mg. | 13 | 3 |
| Phosphorus mg. | 93 | 14 |
| Potassium mg. | 152 | 51 |
| Sodium mg. | 49 | 17 |
| Zinc mg. | 0.38 | 0.17 |
| Vitamins | | |
| Ascorbic Acid mg. | 0.94 | 5.00 |
| Thiamin mg. | 0.038 | 0.014 |
| Riboflavin mg. | 0.162 | 0.036 |
| Niacin mg. | 0.084 | 0.177 |
| Pantothenic Acid mg. | 0.314 | 0.223 |
| Vitamin $B_6$ mg. | 0.042 | 0.011 |

TABLE VIII-continued

Comparison of Cow's Milk With Human Milk

| Per 100 g | Cow | Human |
|---|---|---|
| Folic Acid mcg. | 5 | 5 |
| Vitamin $B_{12}$ mcg. | 0.357 | 0.045 |
| Vitamin A I.U. | 126 | 241 |
| Cholesterol mg. | 14 | 14 |

TABLE IX

Protein Composition Of (Cow & Human Milk) g/100 g

| Protein | Cow | Human |
|---|---|---|
| Casein (total) | 2.6 | 0.32 |
| β-Lactoglobulin | 0.32 | Negligible |
| α-Lactalbumin | 0.12 | 0.28 |
| Serum albumin | 0.04 | 0.06 |
| Lysozyme | Negligible | 0.04 |
| Lactoferrins | 0.02 | 0.20 |
| Immunoglobulins | 0.07 | 0.10 |

A ratio of the various whey proteins between cow's and human milk is presented in Table X.

TABLE X

Ratio Of Various Whey proteins in Cow's & Human Milk

| Protein | Cow's Milk (g/100 g) | % (1) | Human Milk | % | Ratio H/C (2) | 1 × 2 | Mix Composition |
|---|---|---|---|---|---|---|---|
| α-La | 0.12 | 48 | 0.28 | 43.75 | 2.33 | 1.10 | 43.5 |
| L-Fe | 0.02 | 8 | 0.20 | 31.25 | 10 | 0.80 | 31.6 |
| IgG | 0.07 | 28 | 0.10 | 15.63 | 1.43 | 0.39 | 15.4 |
| BSA | 0.04 | 16 | 0.06 | 9.37 | 1.5 | 0.24 | 9.5 |

As shown in the foregoing tables, cow's milk contains 3.3% protein while human milk has only 1%. Caseins are the major protein components in cow's milk (about 77% of total protein) whereas human milk contains a high ratio of whey proteins to caseins (about 2:1). β-Lactoglobulin concentration in cow's milk is the highest of the whey proteins while it is negligible in human milk similarly, lactoferrin is ten times higher in concentration in human milk than in cow's milk. Immunoglobulin and serum albumin concentrations are about 1.5 times higher in human milk than in cow's milk.

In the infant formula of the present invention, lactose and fat levels are adjusted to simulate human milk. Vegetable fat replaces butter fat. Casein to whey ratio is also reduced to simulate human milk. Other additives and supplements such as vitamins, taurine, and minerals may be included if desired. The total solute load is reduced to the level found in human milk.

To achieve this objective, whey protein fractions obtained from the fractionation and elution in accordance with the process of this invention, were first combined in the ratio shown in Table XI below.

TABLE XI

Dietary Formulation A

| α-Lactalbumin fraction | 43.5% |
|---|---|
| Lactoferrin fraction | 31.6% |

TABLE XI-continued

Dietary Formulation A

| Immunoglobulin fraction | 15.4% |
|---|---|
| Bovine serum albumin fraction | 9.5% |

The above whey protein mix was then incorporated into a human milk-like formulation with the composition shown in Table XII.

TABLE XII

Infant Formula

| Ingredient | | Liquid formula (g/100 g) | Dry Formula Base (g/6 oz liquid) |
|---|---|---|---|
| Water | | 87.20 | 0 |
| β-Casein | | 0.28 | 0.504 |
| κ-Casein | | 0.04 | 0.072 |
| Prepared whey protein mix | α-La, BSA, L-Fe, Ig-G → | 0.64 | 1.152 |
| Lysozyme | | 0.04 | 0.072 |

TABLE XII-continued

Infant Formula

| Ingredient | Liquid formula (g/100 g) | Dry Formula Base (g/6 oz liquid) |
|---|---|---|
| Lactoperoxidase | 750 (activity) | 1350 |
| Fat | 4.5 | 8.1 |
| Lactose | 7.0 | 12.6 |
| Ash | 0.2 | 0.36 |

The liquid mix prepared according to the above composition contained about 2% total solids, (of which salts from the eluting buffers comprise 90% and total proteins comprise about 10%), and 98% water. This liquid mix was then concentrated through a 10,000 molecular weight cut-off, spiral ultrafiltration membrane to 5–15% total proteins, followed by diafiltration with distilled water at 0.5–1.0× to remove remaining salt residues. This formulation may be further concentrated by processes normally utilized in the treatment of labile proteins, such as ultrafiltration, reverse osmosis, freeze drying, freeze concentration, spray drying and the like or any combination thereof. The formulations of this invention may be further fortified with suitable additives and fortifiers. Such additives and fortifiers include but are not limited to nonfat milk solids, vegetable solids, carbohydrate sweeteners, minerals and vitamins. The solid composition of one exemplary formulation of the present invention is presented in Table XIII.

TABLE XIII

Solid Composition Of One Exemplary Formulation Of The Present Invention

| Ingredients | gm/16 oz of Formula Powder |
|---|---|
| Proteins: | |
| Casein Hydrolysate | 11.00 |
| α-Lactalbumin | 9.63 |
| Bovine Serum Albumin | 2.06 |
| Lactoferrin | 6.88 |
| Immunoglobulins | 3.44 |
| Lysozyme | 1.38 |
| Fat | |
| Coconut Oil | 53.56 |
| Sunflower Oil | 46.08 |
| Corn Oil | 36.79 |
| Butter Fat | 14.10 |
| Carbohydrate: | 236.95 |
| Lactose | |
| Moisture (Water Content): | 15.20 |
| Linoleic Acid: | 2.41 |
| Vitamins: | |
| Vit. A | 8288 (IU) |
| Vit. D | 1720 (IU) |
| Vit. E (tocopherol) | 86 (IU) |
| Vit. K | 0.0003 |
| Vit. B1 | 0.0018 |
| Vit. B2 | 0.0012 |
| Vit. B6 | 0.0004 |
| Vit. B12 | 0.0000002 |
| Vit. C (ascorbic acid) | 0.17 |
| Niacin | 0.006 |
| Folic Acid | 0.0001 |
| Pantothenic Acid | 0.008 |
| Biotin | 0.0001 |
| Choline | 0.34 |
| Inositol | 0.18 |
| Minerals: | |
| Calcium | 1.10 |
| Phosphorus | 0.48 |
| Magnesium | 0.10 |
| Iron | 0.001 |
| Zinc | 0.006 |
| Manganese | 0.0003 |
| Copper | 0.003 |
| Iodine | 0.0003 |
| Sodium | 0.59 |
| Potassium | 1.76 |
| Chloride | 2.06 |
| Cholesterol | 0.48 |

EXAMPLE 10
Formulations As Fat Substitutes

β-lactoglobulin exhibits high water-binding qualities and α-lactalbumin increases viscosity and also absorbs a high content of fats and oils because of these properties, a combination of these proteins would lend itself to use as fat substitutes. This product when incorporated in appropriate proportions into some food products improves the quality and characteristics of the product and may be used as a fat substitute.

β-lactoglobulin elutes, and along with IgG, as fraction 2 in the process of the present invention and α-lactalbumin is eluted in fraction 3. IgG is separated from the β-lactoglobulin fraction as described in Example 7 and is mixed with the α-lactalbumin fraction in a 60 and 40% ratio. The mix of the two proteins (β-La+α-La) is passed through a 10,000 molecular weight cut-off ultra-filtration membrane at 40° F. with a differential pressure of 10 psi and the permeate, consisting of water and soluble salts, is removed until a 40-50% total solids concentration is achieved. This is followed by a diafiltration at 0.5× with distilled water to remove remaining salt residues. The concentrated and purified mix thus obtained may be frozen, freeze-dried, chilled or dehydrated for further use. Other additives such as flavor enhancers, vitamins and sweeteners may be included in these formulations as desired.

It has thus been shown that the present invention provides a method for the continuous and sequential separation of whey proteins and formulation of the eluted fractions which may be used as food additives or substitutes.

The foregoing description of the preferred embodiments of the subject invention have been presented for purposes of illustration and description and for a better understanding of the invention. It is not intended to be exhaustive or to limit the invention to the precise form disclosed; and, obviously, many modifications and variations are possible in the light of the above teaching. The particular embodiments were chosen and described in some detail to best explain the principles of the invention and its practical application thereby to enable others skilled in the relevant art to best utilize the invention in various embodiments and with various modifications as are suited to the particular use contemplated. It is intended that the invention be defined by the claims appended hereto.

What is claimed is:

1. A method for the sequential separation of whey proteins, comprising the steps of:

a) packing a chromatographic column with a cationic exchange resin to provide a packed chromatographic column;

b) equilibrating said packed chromatographic column with a buffer;

c) providing a whey sample containing whey proteins comprising lactoferrin, immunoglobulin, -lactoglobulin, -lactalbumin, and bovine serum albumin;

d) passing said whey sample through said packed chromatographic column under conditions whereby at least a portion of said whey proteins adsorb to said packed chromatographic column;

e) washing said packed chromatographic column with a buffer;

f) sequentially eluting immunoglobulin and -lactoglobulin from said packed chromatographic column with a buffer;

g) reconditioning said packed chromatographic column with a buffer;

h) eluting -lactalbumin from said packed chromatographic column with a buffer;

i) reconditioning said packed chromatographic column with a buffer;

j) eluting bovine serum albumin from said packed chromatographic column with a buffer; and k) eluting lactoferrin from said packed chromatographic column with a buffer to create an eluate containing lactoferrin.

2. The method of claim 1, wherein said whey is selected from the group consisting of pasteurized sweet whey, pasteurized acid whey, non-pasteurized acid whey, and whey protein concentrate.

3. The method of claim 1, wherein said chromatographic column is a radial flow column.

4. A method for the separation of -lactoglobulin from whey proteins, said method comprising the steps of:

a) packing a radial flow chromatographic column with an anion exchange resin to provide a first packed chromatographic column;

b) equilibrating said first packed chromatographic column with a buffer;

c) providing a whey sample containing whey proteins comprising lactoferrin, immunoglobulin, -lactoglobulin, -lactalbumin, and bovine serum albumin;

d) passing said whey sample through said first packed chromatographic column under conditions wherein -lactoglobulin adsorbs to said first packed chromatographic column and a permeate flows through said first packed chromatographic column;

e) collecting said permeate from said first packed chromatographic column, wherein said permeate comprises -lactalbumin, immunoglobulin, bovine serum albumin and lactoferrin;

f) eluting said adsorbed -lactoglobulin from said first packed chromatographic column with a buffer to produce an eluate;

g) packing a second chromatographic column with a cation exchange resin to provide a second packed chromatographic column;

h) equilibrating said second packed chromatographic column;

i) passing said permeate from said first packed chromatographic column through an ultrafiltration membrane to produce an ultrafiltrate;

j) passing said ultrafiltrate through said second packed chromatographic column, under conditions such that immunoglobulin, -lactalbumin, bovine serum albumin and lactoferrin adsorb to said second packed chromatographic column;

k) eluting said immunoglobulin from said second packed chromatographic column with a buffer;

l) reconditioning said second packed chromatographic column with a buffer;

m) eluting said -lactalbumin from said second packed chromatographic column with a buffer;

n) reconditioning said second packed chromatographic column with a buffer;

o) eluting said bovine serum albumin from said second packed chromatographic column with a buffer; and p) eluting said lactoferrin from said second packed chromatographic column with a buffer.

5. The method of claim 4, wherein said second packed chromatographic column is radial flow column.

6. The method of claim 4, wherein said permeate is combined with said eluate obtained at step f) to produce a fat substitute.

7. The method of claim 6, wherein said fat substitute comprises about 60% said eluate and 40% said permeate.

8. The method of claim 4, further comprises combining said α-lactalbumin, immunoglobulin, and said bovine serum albumin to produce an infant formula.

9. The method of claim 8, wherein said infant formula further comprises at least 25% of said lactoferrin and less than one half of a percent of β-lactoglobulin.

10. The method of claim 9, wherein said infant formula further comprises casein hydrolysate, fat, nonfat milk solids, carbohydrate, minerals, and vitamins.

11. The method of claim 8, wherein said infant formula further comprises about 43.5% of said α-lactalbumin eluted from said second packed chromatography column at step m), about 31.6% lactoferrin eluted at step p), about 15.4% immunoglobulin eluted at step k), and about 9.5% bovine serum albumin eluted at step o).

\* \* \* \* \*